(12) United States Patent
Bierer et al.

(10) Patent No.: US 10,336,974 B2
(45) Date of Patent: Jul. 2, 2019

(54) BIOGAS PLANT SERVICE DEVICE

(75) Inventors: Johann Bierer, Dorfen (DE); Matthias Rabener, Oelde (DE); Andreas Czwaluk, Vechta (DE)

(73) Assignee: UTS BIOGASTECHNIK GMBH, Hallbergmoos (DE)

( * ) Notice: Subject to any disclaimer, the term of this patent is extended or adjusted under 35 U.S.C. 154(b) by 1293 days.

(21) Appl. No.: 13/145,658

(22) PCT Filed: Jan. 21, 2010

(86) PCT No.: PCT/EP2010/000346
§ 371 (c)(1),
(2), (4) Date: Aug. 18, 2011

(87) PCT Pub. No.: WO2010/084003
PCT Pub. Date: Jul. 29, 2010

(65) Prior Publication Data
US 2012/0122200 A1    May 17, 2012

(30) Foreign Application Priority Data

Jan. 21, 2009 (DE) .................. 10 2009 005 628
Jul. 20, 2009 (DE) .................. 10 2009 034 127

(51) Int. Cl.
*C12M 1/00* (2006.01)
*C12M 1/107* (2006.01)

(52) U.S. Cl.
CPC ............ *C12M 23/00* (2013.01); *C12M 21/04* (2013.01); *Y02E 50/343* (2013.01)

(58) Field of Classification Search
CPC ...... C12M 21/04; C12M 23/00; C12M 23/56; C12M 27/02; Y02E 50/343;
(Continued)

(56) References Cited

U.S. PATENT DOCUMENTS 1,448,391 A * 3/1923 Cromer ................... 435/279
4,166,835 A * 9/1979 Anderson .......... C05F 17/0018
210/DIG. 9
(Continued)

FOREIGN PATENT DOCUMENTS

DE    40 15 478       9/1991
DE    19714342    *  1/1998
(Continued)

OTHER PUBLICATIONS

English translation of EP1717305.*
(Continued)

*Primary Examiner* — Kevin Joyner
*Assistant Examiner* — Holly M Mull
(74) *Attorney, Agent, or Firm* — Greer, Burns & Crain, Ltd.

(57) ABSTRACT

A biogas plant service device and an associated biogas plant with a service shaft for biogas plants includes a fermentation tank with a tank wall, a fermentation tank interior and a tank cover covering the fermentation tank interior. The service shaft has a service opening to carry out the assembly, disassembly and maintenance of the plant, such as, a stirrer. The service shaft is arranged on a tank roof covering the fermenter tank interior for sealing the tank roof. An assembly rod is provided extending into the fermentation mass in the fermentation tank interior from the service shaft and at a distance from the tank wall. The service shaft is fixed to a support frame which has a support section, with a fixing apparatus provided on the support section by means of which the support section can be aligned and fixed outside the fermentation tank interior.

14 Claims, 3 Drawing Sheets

(58) Field of Classification Search
CPC .............. B01F 13/0049; B01F 15/0201; B01F 2003/125; B01F 7/00591; B01F 7/161; C02F 3/28; G21C 19/02; G21C 19/10; Y10S 210/09; C04F 3/28
USPC ................................ 435/298.1, 300.1, 289.1
See application file for complete search history.

(56) References Cited

U.S. PATENT DOCUMENTS

| | | | | |
|---|---|---|---|---|
| 4,293,412 A | * | 10/1981 | Lescure | .................... C02F 3/28 210/179 |
| 5,426,024 A | * | 6/1995 | Flores-Cotera et al. | .......... 435/3 |

FOREIGN PATENT DOCUMENTS

| | | |
|---|---|---|
| DE | 20 2004 004101 | 9/2004 |
| DE | 69922379 T2 | 12/2005 |
| DE | 202006010384 U1 | 12/2006 |
| DE | 102007005069 A1 | 7/2008 |
| EP | 1577376 * | 2/2005 |
| EP | 1717305 | 9/2006 |

OTHER PUBLICATIONS

English translationof EP 1577376 same as DE 20 2004 004 101 submitted by the applicant.*
English abstract of DE19714342.*
English translation of DE19714342.*

* cited by examiner

BIOGAS PLANT SERVICE DEVICE

BACKGROUND

The present invention relates to a biogas plant servicing device having at least one servicing well for at least one fermenter tank of a biogas plant. The servicing well is in particular disposed at a tank cover covering the fermenter tank of the biogas plant. The tank cover is preferably inclined at an angle alpha relative to the horizontal. Use is likewise conceivable with flat roofs or substantially flat roof constructions. The servicing well is in particular configured in a way so as to seal the tank cover and disposed at an inclination corresponding to the inclination of the tank cover.

EP 1 717 305 B1 discloses a biogas plant servicing device or a servicing well for a fermenter tank of a biogas plant wherein the servicing well as a gas-tight cover is mounted dome-like above a servicing opening formed in a fermenter tank cover or in a tank cover through which an agitating unit extends which is guided and retained to be height adjustable at a mounting rod passing through the fermenter tank interior. Moreover the agitating unit can be moved out of the fermenter tank into the servicing well interior. The interior of the servicing well has a closable access opening. The tank cover is configured as a tank cover inclined relative to the horizontal through which the servicing well with a lower well end is guided to be gas-tight, forming the servicing opening and into the fermenter tank interior in which the lower well end is supported on and fixed to a carrying console having a horizontal junction plane and being disposed in the tank interior. Said console in turn is supported on and anchored to the inside surface of the fermenter tank wall via diagonal struts.

This known prior art is functional and fulfills its purpose satisfactorily. It is the object of the present invention to provide a different servicing well or a different servicing device which allow a satisfactory function independently of the indicated patent.

SUMMARY

The biogas plant servicing device according to the invention having at least one servicing well is provided to be used in a biogas plant. A biogas plant suitable therefor comprises at least one fermenter tank having at least one outer tank wall and at least one fermenter tank interior and at least one tank cover covering the fermenter tank interior. The servicing well of the biogas plant servicing device comprises at least one servicing opening to facilitate in particular installation and removal and/or maintenance of devices such as an agitator. The servicing well is to be disposed and it is in particular disposed at a tank cover covering the fermenter tank interior at least in part so as to seal the tank cover. At least one mounting rod is provided projecting into the fermenter tank interior and in particular into the fermenter mass and starting from the servicing well or extending from there into the fermenter tank. The mounting rod is provided to be, or is, disposed spaced apart from the tank wall. The mounting rod can in particular be installed or fastened spaced apart from the tank wall. The servicing well is fastened to at least one supporting stand comprising at least one supporting section. The supporting section is provided with fasteners with which the supporting section can be aligned and fastened external of the fermenter tank interior.

The biogas plant servicing device according to the invention has many advantages. A considerable advantage is that the supporting section does not pass through the tank cover. Attachment to the inner tank wall in the interior of the fermenter tank is not required. This allows saving work considerably.

The invention has the further advantage over the known prior art that the entire mounting fixtures of the servicing well are not exposed to the aggressive ambience within the fermenter tank. In particular does the supporting structure not come into permanent contact with the fermenter mass. This allows to use simpler and less expensive construction materials. Another considerable advantage is that the fermenter mass flow is not affected by the supporting structure.

In the prior art the fastening to the inside surface of the fermenter tank wall in the interior of the fermenter tank is more complicated and it may be more susceptible to trouble due to the aggressive ambience.

The servicing well can in particular comprise at least one working platform providing access to the servicing well. The supporting stand may be configured as a console to which the servicing well is fastened. Then the console may comprise at least one supporting section and at least one working platform providing access to, or comprising, the servicing well.

In all of the configurations the servicing well may be attached to the top of the tank wall or radially outwardly at the outside surface of the tank wall. A radial fastening at the inner tank wall within the interior is not required.

According to the invention, attachment to the inside surface of the tank wall is likewise conceivable above the tank cover on the inside surface of the tank wall. For example in the case that the tank wall extends upwardly above the tank cover. Attachment of the servicing well is then also possible to the inside surface of the tank wall above the tank cover without having the supporting section in permanent contact with the fermenter mass or the generated biogas. In preferred configurations the supporting section is fastened onto the tank wall external of the fermenter tank interior. The supporting section can be fastened onto the outside surface of the tank wall and/or onto the top end of the tank wall and/or above the tank cover onto the inside surface of the tank wall.

The supporting section may be configured and suitable to be embedded in a foundation at its lower end region. The supporting section is in particular configured to be embedded at or adjacent to the outside surface of the tank wall in a foundation which may be connected with, or separate from, the fermenter tank foundation.

Advantageously the supporting stand or the console on the whole is configured such that the working platform and the supporting section are interconnected through at least one reinforcing strut. This ensures that the console has sufficient inherent stiffness e.g. for carrying the servicing well that is oriented at a predetermined spot of the tank cover.

The working platform can preferably be, or is, oriented substantially horizontally. An inclination of the supporting section substantially corresponds to an inclination of the outer tank wall. Preferably the supporting section is disposed approximately vertically at least in portions.

Preferably the tank cover is at least partially configured as a top sheeting or comprises at least one top sheeting. In particular in the case of top sheetings the known supporting structure of the servicing well may reach its limits as regards the bottom surface of the tank cover or top sheeting if the inclination angle of the tank cover or top sheeting is increased. In the case of steep top sheeting gradients the mounting of the servicing well to the inside surface of the tank wall will get complicated. In this regard the construction according to the invention offers substantial freedom of construction.

A particular advantage is that the invention and its more specific embodiments provide a biogas plant servicing device and a servicing well which are particularly stable, exceeding reliable and normal functioning and which due to their construction allow easy adjustment to use for different tank covers or else top sheetings. The servicing well can very readily be adjusted e.g. to predetermined spacings or distances regarded from a wall of the fermenter tank and in particular to different inclination angles of the tank cover.

Preferably the supporting stand as a whole is configured so as to have sufficient inherent stiffness for carrying the servicing well that is oriented at a predetermined spot of the tank cover.

The working platform is in particular aligned substantially horizontally. This facilitates utilization to users. The working platform may immediately follow the supporting section or else may be held spaced apart via an intermediate section. In a preferred configuration the supporting section may be disposed at the outer wall and the servicing well and/or a working platform may extend in transverse on the tank cover. Between the supporting section and the servicing well and/or the working platform an intermediate section may be provided which offers a walkway from the tank wall to the servicing well and/or the working platform. The supporting section may be aligned perpendicular and the working platform, horizontally. The or an intermediate section may assume many different angles.

The supporting section of the supporting stand may preferably be fastened to the tank wall by fasteners such as screws or dowel pins. The supporting area may be fastened at the outside surface of the tank wall or else to the top end of the tank wall. Attachment is also conceivable to the inner tank wall above the tank cover. It is also conceivable for the supporting area to be fastened to a firm roof segment or a firm roof element extending from the tank wall. It is also conceivable to incorporate into the tank wall holders to fasten the supporting stand to.

The supporting section of the supporting console may at its lower end region be embedded in a foundation located on the outside surface of the tank wall in the region of the bottom of the fermenter tank.

On the whole the biogas plant servicing device according to the invention presents the option of subsequently, i.e. to an existing biogas plant, mounting a servicing well in a suitable place of the roof or cover since the servicing well does not require attachment in the interior to an inside surface of a fermenter tank wall. Where biogas plants are referred to according to the invention it should be noted that employing the servicing device with its servicing well is also conceivable with other tanks. Given specific roof constructions such as glass fiber reinforced sheeting or other materials, the tank cover may be accessible on foot.

Preferably an inclination of the supporting section substantially corresponds to an inclination of the outer tank wall. Said supporting section may be disposed in parallel to the tank wall. An approximately vertical arrangement is likewise conceivable. The intermediate section may run in parallel or approximately parallel to the cover inclination.

Preferably the working platform and the supporting section may be connected via at least one, in particular two or more reinforcing struts.

The supporting section may be configured e.g. as an approximately vertical subsection. The supporting section may be provided with means for aligning the supporting section at a suitable distance e.g. in parallel with the outer side of the tank wall.

The servicing well is in particular mounted to a supporting stand configured e.g. as a console which may comprise by way of a subsection a working platform providing access to the servicing well.

The working platform is in particular provided above the tank cover. The tank cover is preferably inclined at an angle alpha relative to the horizontal at least in the region of the servicing well.

The servicing well has in particular at least one servicing opening to facilitate or allow installation and removal, and maintenance of devices such as an agitator or multiple agitators. At least one agitator is provided and in particular at least one agitator is provided at or attached to the mounting rod.

The servicing well in particular comprises at least one adjusting device and in particular at least one height adjusting device and/or at least one lateral adjusting device of the agitating device or the agitator.

At least one servicing opening is in particular provided as a front opening. The servicing opening may comprise a front opening and an additional bottom opening. The front opening is closed e.g. by means of a front panel and the bottom opening, by a bottom panel. The bottom opening is preferably disposed immediately in front of the servicing well and is configured as a closable opening in the tank cover. The front opening and the bottom opening combined form one large servicing opening through which an agitator can be taken from the interior to the exterior. In the maintenance position the or an agitator may be disposed entirely within the servicing well or else when in the maintenance position the agitator is only partially or not at all located within the servicing well.

The servicing well may be provided with at least one viewing window and at least one connecting gas line.

In the region of transition to the tank cover the servicing well is preferably provided with at least one clamping to allow a gas-tight and flexible construction of the connection to the tank cover. It is a matter of course that the entire servicing well interior is preferably configured gas-tight by choosing suitable materials.

The angle alpha of the tank cover inclination preferably lies in the range between 10 and 60 degrees.

The angle alpha of the tank cover inclination relative to the horizontal may be arbitrary and preferably lies in the range between 10 degrees and 60 degrees. A servicing device at a large gradient angle, e.g. 45 degrees, 60 degrees and more is actually only made possible by the supporting construction of the servicing well which is configured from outside the fermenter tank.

In this conjunction it has also been found that the tank cover may be configured as an air-supported roof structure, all the more since the gas production process in the fermenter tank always allows to build up an excess pressure relative to the exterior atmosphere.

It has been found very useful to attach an ascending ladder or ascending stairs between the floor located in the region of the outside surface of the tank wall of the fermenter tank and the working platform.

A mounting aid may further be provided in that the console or the supporting stand comprises at least one crane track above the working platform by means of which to guide at least one crane or revolving crane. A usually employed agitator may e.g. have a mass of 260 kg.

The servicing device may provide for the mounting rod to project vertically into the tank interior and in particular into the fermenter mass. Or else an inclined arrangement of the mounting or supporting rod is possible.

The biogas plant according to the invention comprises at least one fermenter tank having at least one outer tank wall and at least one fermenter tank interior and at least one tank cover covering the fermenter tank interior.

At least one biogas plant servicing device having at least one servicing well is provided. The servicing well or at least one servicing well comprises at least one servicing opening to allow to perform in particular installation and removal and/or maintenance of devices such as an agitator. The biogas plant preferably comprises at least one agitator in at least one fermenter tank. The servicing well is disposed at the tank cover covering the fermenter tank interior so as to seal the tank cover. At least one mounting rod is provided which projects into the fermenter tank interior and in particular into the fermenter mass and starts from the servicing well and which is disposed spaced from the tank wall. The servicing well is fastened to at least one supporting stand comprising at least one supporting section. The supporting section is provided with fasteners with which the supporting section is aligned and fixed outside the fermenter tank interior.

In preferred embodiments the biogas plant according to the invention may be equipped with one or multiple of the servicing wells described above. The servicing well can in particular comprise at least one working platform providing access to the servicing well.

Other advantageous features and configurations of the invention can be taken from the following embodiment which will now be described with reference to the enclosed figures.

BRIEF DESCRIPTION OF THE DRAWINGS

These show in.

DETAILED DESCRIPTION

Figures 1A, 1B:
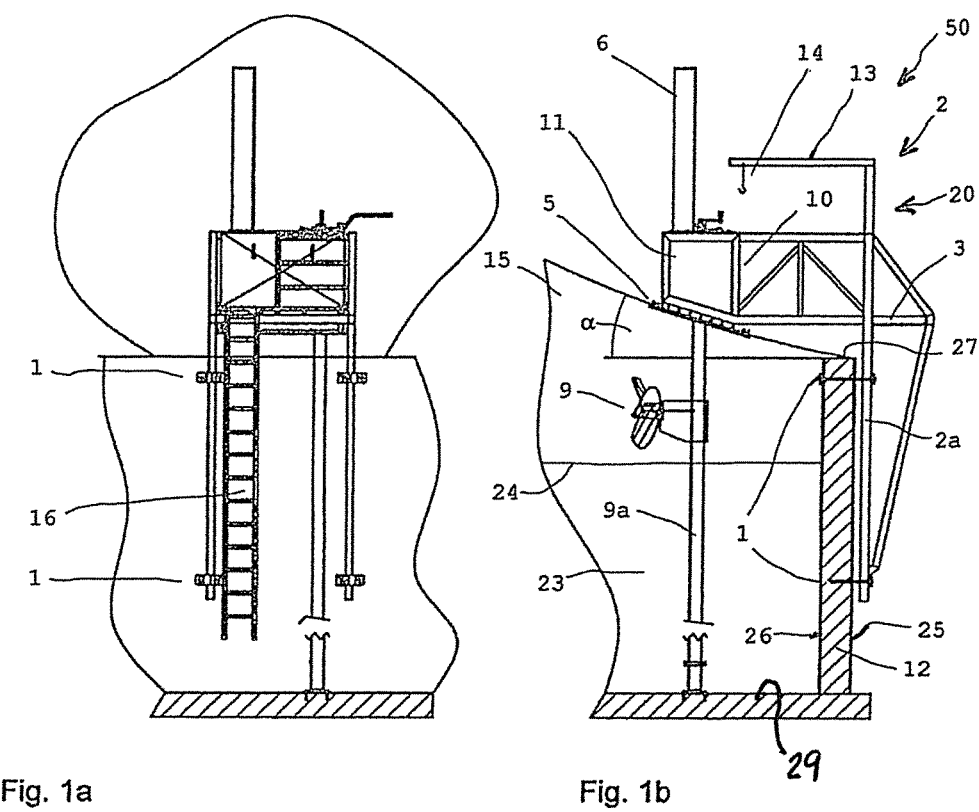
FIG. 1a a servicing well according to the invention in a view from outside the fermenter tank, FIG. 1b a sectional view of the tank wall with a view onto the servicing well.
Figure 1C:
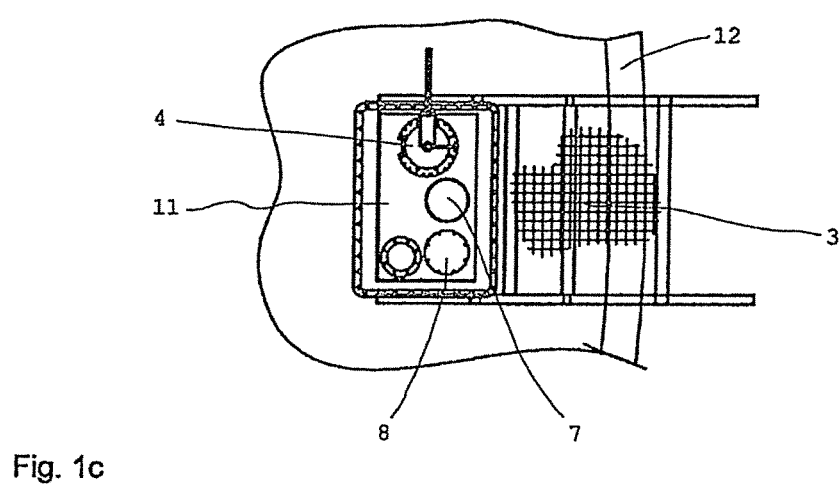
FIG. 1c a top view corresponding to the partial view 1b of a region of the fermenter tank.

FIGS. 1a through 1c illustrate part of a first inventive biogas plant 50 having a biogas plant servicing device 20 comprising a servicing well 11.

The biogas plant 50 comprises a fermenter tank 21 with an interior 22 and a tank wall 12. The interior 22 is upwardly limited by a tank cover 15 which is sealingly attached to the tank wall 12.

The servicing well 11 is provided at the tank cover 15 presently configured as a top sheeting.

The servicing well of the servicing device 20 presently comprises a servicing opening 10 which allows access to or entry into the interior 22 of the fermenter tank 21.

The servicing well is provided with a mounting rod 9a extending from the servicing well inwardly (and possibly outwardly as well). The mounting rod 9a terminates at the bottom end preferably at the bottom 29 of the fermenter tank 21 where it may be rotatably secured. The mounting rod 9a may be oriented vertically or else inclined.

The mounting rod 9a receives at least one agitator 9 which is height-adjustable and laterally pivotal. The agitator 9 may be driven electrically, hydraulically, or in another way. The agitator 9 serves to stir and homogenize the fermenter mass. It is furthermore intended to inhibit deposits and sedimentation. Due to the abrasive and aggressive ambience in the fermenter mass the agitator 9 requires maintenance from time to time. For example the agitator blades must be exchanged as required. In the case of defects the agitator 9 must also be repaired or exchanged.

The agitator 9 is accessible through the servicing opening 10. By way of the height adjusting device 30 of the adjusting device 4 the agitator 9 can be displaced upwardly. Then the agitator 9 is displaced above the surface 24 of the liquid level of the fermenter mass 23 and in particular upwardly as far as the free space in the servicing well 11 above the tank cover 15 or else entirely out into the open for an operator to service or else exchange the readily accessible agitator. The top sheeting 15 does not need to be opened. For servicing, the agitator 9 may likewise be pivoted outwardly from the interior of the servicing well.

The servicing well 11 is fastened to a supporting stand 2 which may, though does not need to, be configured as a console 2. The supporting stand 2 presently comprises a supporting section 2a and a working platform providing access to the servicing well 11. The supporting section 2a is provided with fasteners 1 with which the supporting section 2a is aligned and fastened outside the fermenter tank interior 2.

Said supporting section 2a is fastened outwardly of the fermenter tank interior 22.

The supporting section 2a may in particular be fastened to the outside surface 25 of the tank wall 12 as is shown in FIG. 1. Or else it is possible to fasten the supporting section 2a at the top end or the top surface 27 of the tank wall 12 and/or above the tank cover 15 at the inside surface 26 of the tank wall 12 in case that the tank wall extends upwardly beyond the junction of the tank cover.

In the exemplary embodiment according to FIG. 1 the servicing well 11 is mounted at the outside wall of the fermenter tank 21. Screws and dowel pins in particular serve as fasteners 1 in the exemplary embodiment according to FIG. 1. The screws are screwed into the dowel pins inserted into the outside surface of the tank wall 12 to fasten the console 2 via the supporting section 2a to the outside surface of the tank. It is likewise possible to cast fasteners into the tank wall for example in tanks consisting of concrete or plastic, or else to fix fasteners by welding for tanks partially consisting of metal and in particular steel.

The servicing well 11 is disposed above the cover of the fermenter tank 21. The servicing well 11 is presently mounted to a console 2 as the supporting stand 2.

The console 2 in the present embodiment is substantially rectangular in structure and it is assembled in particular to be sufficiently inherently stiff, e.g. with struts forming triangles or the like and thus making the exemplarily selected frame construction of the console stable.

What is presently the horizontal part of the console 2 forms a working platform 3 providing access to the servicing well 11 which is mounted to and carries the console 2.

A supporting section 2a of the console 2 which in the present embodiment is configured as a vertical subsection can be fastened immediately to the outside surface of a tank wall 12 of the fermenter tank by means of screws or dowel pins 1, as is illustrated in FIG. 1b.

Figures 2A, 2B:
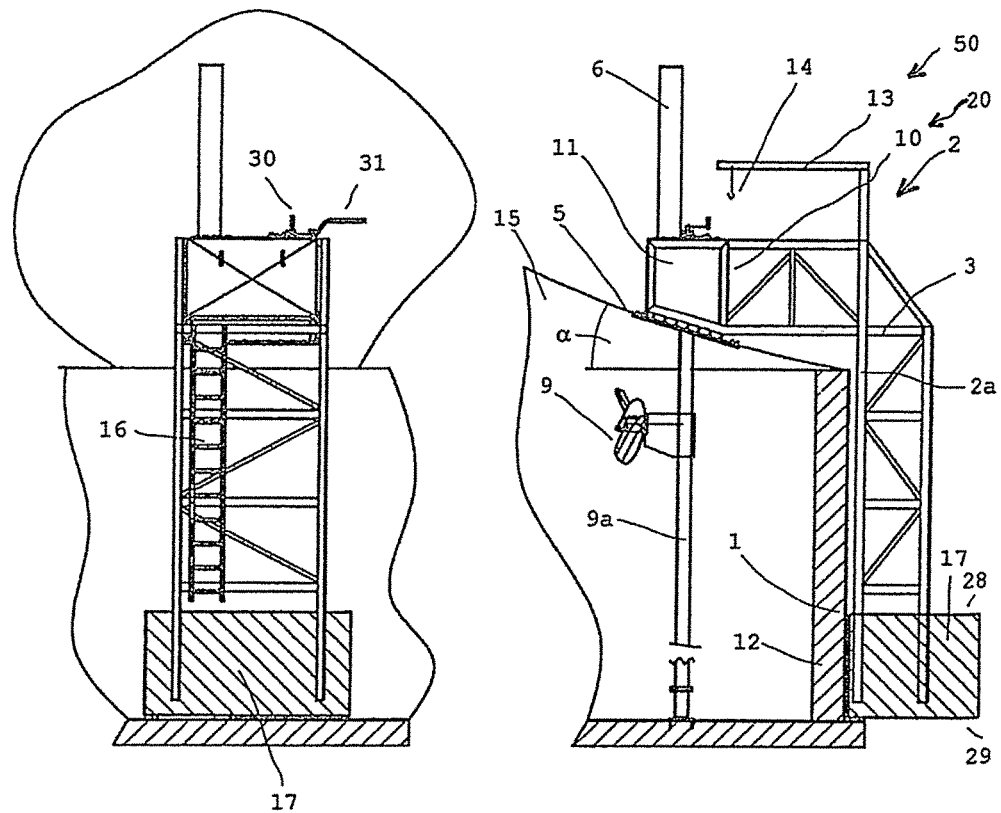
FIG. 2a another servicing well according to the invention in a sectional detail view from outside the fermenter tank.
FIG. 2b a sectional view of the tank wall with a view onto the servicing well.
Figure 2C:
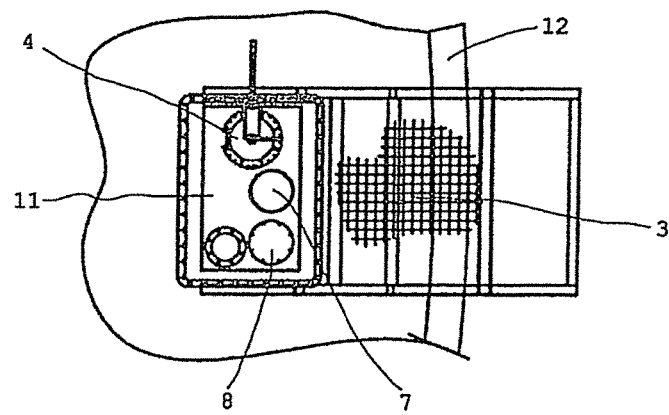
FIG. 2c a top view corresponding to the partial view 2b of a region of the fermenter tank.

The embodiment according to the FIGS. 2a to 2c illustrates another servicing well 11 according to the invention which is disposed above the tank cover of the fermenter tank.

Presently the supporting section 2a is embedded at its lower end region 28 in a foundation 17 located at the outside surface 25 of the tank wall 12 in the region of the bottom 29 of the fermenter tank.

In this embodiment a foundation 17 is provided located for example at the outside surface 25 of the tank wall 12 in the lower region of the outer wall 12 of the fermenter tank 21 or in the region of the bottom 29 of the fermenter tank 21, as is illustrated in FIG. 2a and FIG. 2b. Presently the supporting section 2a of the console 2 is fastened to the foundation 17.

Other suitable foundation placements are conceivable as well. The only thing important is that in this configuration the lower end region 28 of the supporting section 2a of the console 2 can be firmly anchored in the foundation 17, e.g. by way of casting in concrete, such that the inherently rigid structure of the console 2 can offer a stable support for the servicing well 11. It may be important for the mass of the foundation 17 to be sufficiently determined. The console material, in particular the material of the vertical subsection 2a, must then be suitable to be cast in concrete or to be surrounded by a suitable material.

The servicing well 11 itself is configured so as to have a servicing opening which is presently configured as a front opening 10. The front opening 10 allows to perform installation and removal of a device. An agitator 9 or a pump may for example be installed or removed.

The front opening 10 in particular allows maintenance of devices and in particular of the agitator 9. It is provided for the servicing well 11 to comprise a height and lateral adjustment 4 with height adjustment 30 and lateral adjustment 31 of the agitator. This allows ease of exchanging the agitator blades.

It is not required to lower the filling level in the fermenter tank 21. Also, the tank cover does not need to be removed entirely or partially.

At least one connecting or gas line 8 serves for discharging the generated biogas.

The electrically or in particular hydraulically operated agitator 9 is preferably attached to a mounting rod 9a projecting from the servicing well 11 into the fermenter mass. The mounting rod 9a may be disposed vertically.

Maintenance of the installed devices such as the agitator 9 may be done starting from the servicing well 11. Furthermore the installed devices may be checked. This may be done immediately from the working platform 3. During maintenance the agitator 9 may partially or even entirely be located outside the interior of the servicing well.

The fermenting substrate may furthermore be observed through a viewing window which may be located e.g. in the region of the working platform 3.

The servicing well 11 is connected with the sheet of the tank cover 15 to be gas-tight and flexible. To this end a special clamping 5 is provided between the inclined bottom surface of the servicing well 11 and the sheet of the tank cover. The clamping may be adjusted to the cover inclination.

The servicing well 11 itself is intended to be gas-tight when closed, as it is customary in the prior art. Therefore the top surface (facing the cover) of this servicing well 11 is provided with an excess pressure or else an underpressure safety device 6. Between the working platform 3 and the access area of the servicing well 11 the front opening 10 indicated above, such as a door, may be provided having or comprising adequate sealing properties. The bottom of the working platform may be additionally provided with a bottom opening that is normally closed gas-tight by way of a bottom panel, such that when opened the two openings together form the servicing opening through which an agitator 9 can be moved out from the interior 22 above the tank cover to perform maintenance, repairs, or an exchange.

The angle alpha of the cover inclination may be as desired. The embodiments of the invention are particularly preferably directed to any and all, including steep or very steep, cover inclinations.

The tank may consist of a variety of different materials. It is in particular possible and preferred to use fermenter tanks consisting partially or entirely of stone, concrete, metals or metal alloys and in particular steel or other natural substances or plastics. Fermenter tanks consist particularly preferably of concrete or steel. The cover may likewise consist of a variety of different materials. What is particularly preferred is concrete, sheeting, or in particular also steel.

In the case of steep cover gradients the fastening and supporting of the servicing well from the interior of the fermenter tank is relatively complicated. Embodiments according to the invention also allow gradient angles alpha of 30 degrees and more or of 45 degrees and more. Smaller gradients between e.g. 5 degrees and 30 degrees are conceivable as well. Basically, use for a flat roof is conceivable as well. Other than a top sheeting configuration the tank cover may at least in part or else entirely consist of a solid material, such as stone, concrete, or steel.

The tank cover 15 may also be provided as an air-supported roof. The servicing well 11 configured according to the embodiment is particularly suitable therefor since the servicing well 11 is basically not fixed on the wall from inside but at the top of the tank wall or else on the outside.

Working in practice with the servicing well 11 is greatly facilitated with an ascending ladder 16 attached in the region of the outside surface of the tank wall 12 providing access to the working platform 3. Stairs may be provided alternatively.

Presently the working platform has an antiskid grate integrated to increase working safety. The actual mounting operation is furthermore considerably facilitated and assisted with a crane track 13 mounted above the working platform 3 by means of which a crane 14 can be guided.

Figure 3:
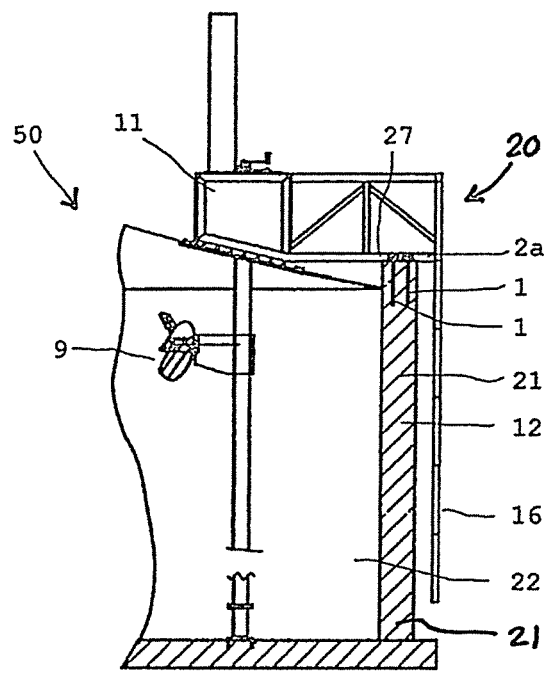
FIG. 3 a sectional view of a fermenter tank of another biogas plant with a third embodiment of a servicing well.

FIG. 3 illustrates a fermenter tank 21 of a biogas plant 50 in a sectional view with the servicing well 11 of the servicing device 20 attached to the top end of the tank wall 12 via the supporting stand 2. To this end the supporting section 2a is in particular directly screwed to the top surface 27 of the tank wall via fasteners 1. A ladder 16 or the like may be provided to facilitate ascension. The further components correspond to those of the preceding embodiments.

Figure 4:
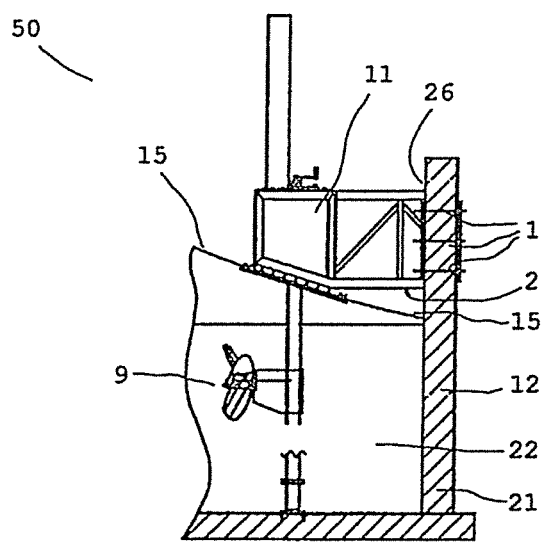
FIG. 4 a sectional view of a fermenter tank of another biogas plant with a fourth embodiment of a servicing well.

FIG. 4 shows another fermenter tank 21 of another biogas plant 50 in a sectional view. The servicing well 11 of the servicing device 20 is attached to the inside surface 26 of the tank wall 12 via the supporting stand 2. The fastening point with the tank wall 12 lies above the tank cover 15 such that the supporting section is fixed and oriented outside the interior 22 of the fermenter tank 21. Presently the tank wall 12 of the fermenter tank 21 extends upwardly beyond the junction of the cover. This enables fastening to the inside surface 26 without having the supporting section continuously exposed to the fermenter mass. Also, there is no impediment to the flow.

Again, a ladder 16 or the like may be provided to facilitate ascension. The further components again correspond to those of the preceding embodiments.

The invention on the whole provides a low-cost, easy to mount servicing device which offers great advantages for all types of roofs or covers.

The enclosed figures show attachments to the tank wall or to the tank foundation. A separate foundation detached from the tank is likewise conceivable.

The servicing well is suitable for any tank cover 15 and any cover inclination and may be retrofitted to virtually any cover or roof 15.

Further configurations and features may be realized as is described in the European patent EP 1 717 305 B1, reference to which is made in this respect.

The invention may be utilized with fermenter tanks of biogas plants. Utilization for other tanks is likewise possible. While the top cover may also be configured hard-wearing and thus accessible on foot, it may be configured as a thin plastic sheet or the like.

The working platform 3 serves for servicing and checking the installed devices 9 and for observing the fermentation substrate through the viewing window 7.

The invention claimed is:

1. A biogas plant assembly comprising:
at least one fermenter tank having at least one tank wall, a fermenter tank interior and a tank cover having an opening, wherein at least part of said at least one fermenter tank extends above ground level and the tank cover is a top sheeting that covers the fermenter tank interior;
a supporting stand including a working platform and a supporting section extending from said working platform, said supporting section being oriented and attached to said at least one tank wall outside of the fermenter tank interior;
at least one servicing well mounted to said working platform, wherein said working platform is independent of and removably mounted on the tank cover and disposed on and sealing the tank cover, wherein said working platform and said servicing well each comprise a servicing opening that are aligned with the opening in the tank cover to facilitate access to the fermenter tank interior and enable at least one of installation, removal and maintenance of devices in the at least one fermenter tank; and
at least one mounting rod projecting from said at least one servicing well into the fermenter tank interior and into a fermenter mass, wherein the at least one mounting rod is spaced from the at least one tank wall.

2. The biogas plant assembly according to claim 1, wherein the supporting section at its lower end region is embedded in a foundation located on an outside surface of the at least one tank wall in the region of a bottom wall of the fermenter tank.

3. The biogas plant assembly according to claim 1, wherein the working platform and the supporting section are connected through at least one reinforcing strut so that the supporting stand has sufficient inherent stiffness for carrying the servicing well oriented at a predetermined spot on the tank cover.

4. The biogas plant assembly according to claim 1, wherein the working platform is oriented horizontally and/or wherein an inclination of the supporting section corresponds to an inclination of the outer tank wall, the supporting section is arranged approximately vertical.

5. The biogas plant assembly according to claim 1, wherein the tank cover is at least partially configured as an air-supported roof.

6. The biogas plant assembly according to claim 5, wherein the working platform is connected with the top sheeting by clamping means to form a gas-tight and flexible seal with the top sheeting.

7. The biogas plant assembly according to claim 1, wherein the tank cover is inclined at an angle alpha relative to a horizontal in the region of the servicing well.

8. The biogas plant assembly according to claim 7, wherein the angle alpha is between 10 and 60 degrees.

9. The biogas plant assembly according to claim 1, wherein at least one agitator is provided at and attached to the at least one mounting rod.

10. The biogas plant assembly according to claim 9, wherein the at least one servicing well comprises at least one height adjusting device or a lateral adjusting device of the at least one agitator.

11. The biogas plant assembly according to claim 1, wherein the at least one servicing well comprises at least one viewing window and at least one connecting gas line.

12. The biogas plant assembly according to claim 1, wherein at least one ascension device consisting of an ascension ladder or ascension stairs are attached to an outside surface of the at least one tank wall of the fermenter tank.

13. The biogas plant assembly according to claim 1, wherein said supporting stand comprises at least one crane track above said servicing opening by means of which at least one crane can be guided.

14. The biogas plant assembly according to claim 1, wherein said tank cover extends at or above a liquid level of the fermenter mass stored in the at least one fermenter tank.

* * * * *